United States Patent
Yamazaki et al.

(10) Patent No.: US 8,936,754 B2
(45) Date of Patent: Jan. 20, 2015

(54) AUTOMATIC ANALYSIS DEVICE

(75) Inventors: Isao Yamazaki, Ryugasaki (JP); Hiroaki Ishizawa, Hitachinaka (JP); Sakuichiro Adachi, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 131 days.

(21) Appl. No.: 13/129,812

(22) PCT Filed: Nov. 12, 2009

(86) PCT No.: PCT/JP2009/069291
§ 371 (c)(1),
(2), (4) Date: Jun. 1, 2011

(87) PCT Pub. No.: WO2010/055890
PCT Pub. Date: May 20, 2010

(65) Prior Publication Data
US 2011/0223066 A1     Sep. 15, 2011

(30) Foreign Application Priority Data

Nov. 17, 2008  (JP) ................................. 2008-293544

(51) Int. Cl.
| | | |
|---|---|---|
| *G01N 21/31* | (2006.01) | |
| *G01N 21/27* | (2006.01) | |
| *G01N 21/17* | (2006.01) | |
| *G01N 21/62* | (2006.01) | |
| *G01N 21/82* | (2006.01) | |
| *G01N 35/02* | (2006.01) | |

(52) U.S. Cl.
CPC .............. *G01N 21/274* (2013.01); *G01N 21/17* (2013.01); *G01N 21/62* (2013.01); *G01N 21/27* (2013.01); *G01N 2201/1293* (2013.01); *G01N 21/82* (2013.01); *G01N 35/025* (2013.01); *G01N 2201/129* (2013.01)

USPC ........ 422/82.05; 422/400; 422/402; 422/403; 422/63; 422/64; 436/45; 436/165; 356/436; 356/328

(58) Field of Classification Search
CPC .................. G01N 21/17; G01N 21/27; G01N 2201/1293; G01N 21/62
See application file for complete search history.

(56) References Cited

U.S. PATENT DOCUMENTS

| | | | |
|---|---|---|---|
| 4,267,572 A | 5/1981 | Witte | |
| 6,882,425 B1 | 4/2005 | Elsenhans et al. | |
| 2008/0020481 A1 | 1/2008 | Yamamoto et al. | |

FOREIGN PATENT DOCUMENTS

| | | |
|---|---|---|
| CN | 101151534 | 3/2008 |
| JP | 54-84781 A | 7/1979 |

(Continued)

OTHER PUBLICATIONS

Office Action issued Aug. 22, 2012 in German Patent Application No. 11 2009 002 702.4.

*Primary Examiner* — P. Kathryn Wright
(74) *Attorney, Agent, or Firm* — Miles & Stockbridge P.C.

(57) ABSTRACT

There is provided a high-accuracy automatic analysis device achieving both of measurement in a wide concentration range and high sensitivity at a low concentration. The signals of a plurality of wavelengths $\lambda 1$ to $\lambda 12$ where the sensitivity of light absorption caused by fine particles is high from a light source 40 are converted to absorbances by a spectroscopic optical system (detector) 41. The absorbances are converted to a secondary parameter from in which a noise component is cancelled by using a previously-defined conversion table 54, so that a concentration of a measured material (predetermined component) is calculated by an operation unit (calculating means) 53 based on the secondary parameter. Thus, analysis being resistant to the noise even at the low concentration can be achieved in a range up to a high concentration.

4 Claims, 5 Drawing Sheets

(56) References Cited

FOREIGN PATENT DOCUMENTS

| | | |
|---|---|---|
| JP | 60-196669 A | 10/1985 |
| JP | 61-82169 A | 4/1986 |
| JP | 62-179639 A | 8/1987 |
| JP | 02-085745 A | 3/1990 |
| JP | 08-075740 A | 3/1996 |
| JP | 08-219984 A | 8/1996 |
| JP | 2003-502631 A | 1/2003 |
| JP | 2009-126639 A | 6/2009 |
| WO | WO 00/77494 A1 | 12/2000 |
| WO | WO 2006/104006 A1 | 10/2006 |

AUTOMATIC ANALYSIS DEVICE

TECHNICAL FIELD

The present invention relates to an automatic analysis device for automatically analyzing a component of blood or others.

BACKGROUND ART

As a method widely used in automatic analysis for blood, absorption photometry is known. In the absorption photometry, light is irradiated to a reaction solution prepared by mixing a biological sample with a reagent in a reaction container, an absorbance which is the attenuation of light having a specific wavelength is measured, and a concentration of a component of an analysis object is calculated from a relationship between the absorbance and the concentration. In many cases, a direct (linear) proportional relationship is established between the concentration and the absorbance of the component.

In the absorption photometry, as a technique of reducing influence of the noise caused by air bubbles or others in the reaction container on an analysis result, it is known to measure an absorbance of a sub wavelength in addition to the absorbance having the specific wavelength and calculate the concentration by using a difference between both absorbances or a ratio therebetween.

Moreover, in the absorption photometry, as a method used particularly for analyzing a minor component, a method of measuring the component based on light absorption due to aggregation substances such as latex agglutination and immunonephelometry is known. For example, in the immunonephelometry, a degree of aggregation of particles of an immune complex formed of a specific component and an antibody whose antigen is the specific component is analyzed by measuring an absorbance, so that the concentration of the specific component is calculated. In the latex agglutination, with using a reagent containing latex particles coated with antibodies directed to a specific component, a degree of aggregation of the latex particles is analyzed by measuring an absorbance, so that the concentration of the specific component is calculated.

Also in these methods, the influence of the noise can be often reduced by using the difference between the absorbances measured at two wavelengths or the ratio therebetween. However, in this case, a range where the concentration and the absorbance of the component are on the linear relationship is small. Therefore, in order to measure a concentration in a wide range, appropriate particle size, concentration, and wavelength are selected, and, for example, a spline function is used for a calibration curve instead of a straight line.

Patent Document 1 proposes a method in which, in order to reduce an analysis cost in the immunonephelometry, calibration curves having linear relationships at a plurality of wavelengths are previously obtained, and the calibration curves are switched depending on the concentration so that the shortest wavelength not causing the prozone effect is selected. According to the method, there is an effect that a linear calibration curve can be used even in the immunonephelometry.

Patent Document 2 proposes a technique in which, in order to reduce the influence of the noise, a plurality of items are measured at the same time by using measurement values of absorbances at three or more wavelengths. According to the technique, influence of a noise component having a wavelength dependency such as a serum color on an analysis result or others can be prevented.

Patent Document 3 proposes a technique in which, in order to improve the measurement accuracy in the latex agglutination, change from an absorbance at a reference measurement point to an absorbance at a measurement point within a range of a threshold value is obtained by the least square method. According to the technique, highly accurate measurement can be achieved even when an absorbance of a sample cannot be measured.

PRIOR ART DOCUMENTS

Patent Documents

Patent Document 1: Japanese Patent Application Laid-Open Publication No. H08-75740
Patent Document 2: Japanese Patent Application Laid-Open Publication No. H02-85745
Patent Document 3: Japanese Patent Application Laid-Open Publication No. H08-219984

DISCLOSURE OF THE INVENTION

Problems to be Solved by the Invention

However, in the above-described conventional techniques, in the case of the analysis by the latex agglutination, when the measurement is performed by setting a reagent and a wavelength so as to measure a high concentration of a measured component, change of an absorbance at a low concentration is small and is easily affected by the noise, and therefore, there is a problem that it is difficult to increase sensitivity in a wide concentration range.

In the proposition of Patent Document 1, since the used wavelength is switched depending on the concentration, the range of the concentration can be expanded to some extent. However, for practical use, there is a problem that a gap between the calibration curves is caused at a change point of the concentration or others. Moreover, the noise reduction at a low concentration is insufficient.

In the proposition of Patent Document 2, the influence of the noise having the wavelength dependency can be reduced by using the three or more wavelengths. However, the number of wavelengths mainly contributing to the measurement of the signal component is one, and therefore, in the latex agglutination, high-sensitive measurement cannot be achieved in the wide concentration range.

In the proposition of Patent Document 3, the change in the absorbance is calculated by using the least square method. However, the wavelength is fixed, and therefore, the high-sensitivity measurement cannot be achieved in the wide concentration range.

The present invention has been made in consideration of the above-described problems, and a preferred aim of the present invention is to provide a high-accuracy automatic analysis device achieving both of the measurement in the wide concentration range and the high sensitivity at the low concentration.

The above and other preferred aims and novel characteristics of the present invention will be apparent from the description of the present specification and the accompanying drawings.

Means for Solving the Problems

The typical ones of the inventions disclosed in the present application will be briefly described as follows.

An automatic analysis device of the present invention includes: a plurality of reaction containers; a sample probe for discharging a sample into the reaction container; a reagent probe for discharging a reagent into the reaction container into which the sample has been discharged; a light source for irradiating light to the reaction container into which the sample and the reagent have been discharged; a detector for detecting light having a plurality of wavelengths transmitted from the light source through the reaction container; and calculating means for calculating a concentration of a predetermined component in the sample by using signals of the plurality of wavelengths in the detector and based on a relationship between the concentration and a secondary parameter which is converted by using a previously-defined conversion table or conversion expression.

It is preferred that each of the signals of the plurality of wavelengths is converted to an absorbance, and then, is converted to the secondary parameter calculated by using a value of the absorbance at each of the plurality of wavelengths.

It is preferred that a wavelength dependency of the absorbance is expressed by synthesis of a function for expressing a wavelength dependency of a signal component and a function for expressing a wavelength dependency of a noise component.

It is preferred that the synthesis is expressed by linear combination of the function for expressing the wavelength dependency of the signal component and the function for expressing the wavelength dependency of the noise component, and a coefficient of each of the functions for expressing the wavelength dependencies is obtained by the least square method.

It is preferred that, in the wavelength dependency of the signal component, a coefficient of the wavelength is expressed by a negative exponential function.

It is preferred that the coefficient is set to a different value depending on a type of the measurement.

It is preferred that the wavelength dependency of the noise component is expressed by a constant value with respect to the wavelength.

It is preferred that a measurement value at a wavelength where the absorbance is higher than a previously-determined value is not used for calculating the concentration of the predetermined component.

It is preferred that, for an absorbance difference obtained by subtracting a value of an absorbance at a predetermined wavelength from the value of the absorbance at each of the plurality of wavelengths, the secondary parameter is calculated by using a gain function and a weighting function depending on the plurality of wavelengths.

It is preferred that the weighting function is changed so as to be small at wavelengths where the absorbance is relatively large and small, and to be large at a wavelength between the wavelengths where the absorbance is large and small.

It is preferred that the gain function is expressed by an exponential function of the wavelength.

It is preferred that the coefficient of the wavelength is set to a different value depending on a type of the measurement.

It is preferred that a plurality of times of the measurement are performed in a process of reaction progress in the reaction container, and a relationship between the concentration and a value, a changed amount, or a change gradient of the secondary parameter obtained in each time of the measurement is previously examined, so that the concentration of the predetermined component in the sample is calculated based on the relationship.

It is preferred that an item analyzed by the calculating means and an item not analyzed by the calculating means are divided for each analyzed item.

It is preferred that the item analyzed by the calculating means is an item obtained by measuring the concentration of the predetermined component based on the light absorption caused by the aggregation substances containing the predetermined component.

Also, another automatic analysis device of the present invention includes: a plurality of reaction containers; a sample probe for discharging a sample into the reaction container; a reagent probe for discharging a reagent into the reaction container into which the sample has been discharged; a light source for irradiating light to the reaction container into which the sample and the reagent have been discharged; a detector for detecting light having a plurality of wavelengths transmitted from the light source through the reaction container; and calculating means for calculating a concentration of a predetermined component in the sample by using absorbances at the plurality of wavelengths based on light absorption caused by aggregation substances containing the predetermined component and an absorbance at a wavelength on which a noise component is reflected.

It is preferred that a measurement value at a wavelength where the absorbance is higher than a previously-determined value is not used for calculating the concentration of the predetermined component.

Effects of the Invention

The effects obtained by typical aspects of the present invention will be briefly described below.

That is, the concentration of the predetermined component in the sample is calculated by using signals of the plurality of wavelengths in the detector and based on the relationship between the concentration and the secondary parameter which is converted by using the previously-defined conversion table or conversion expression. In other words, the concentration is calculated by combining the signals of the plurality of wavelengths where the sensitivity for fine particles is high, and therefore, the analysis can be performed at high accuracy from the low concentration to the high concentration.

In this manner, the high-accuracy automatic analysis device achieving both of the measurement in the wide concentration range and the high sensitivity at the low concentration can be provided.

BEST MODE FOR CARRYING OUT THE INVENTION

Hereinafter, embodiments of the present invention will be described in detail with reference to the accompanying drawings. Note that components having the same function are denoted by the same reference symbols throughout the drawings for describing the embodiment, and the repetitive description thereof will be omitted as much as possible.

Figure 1:
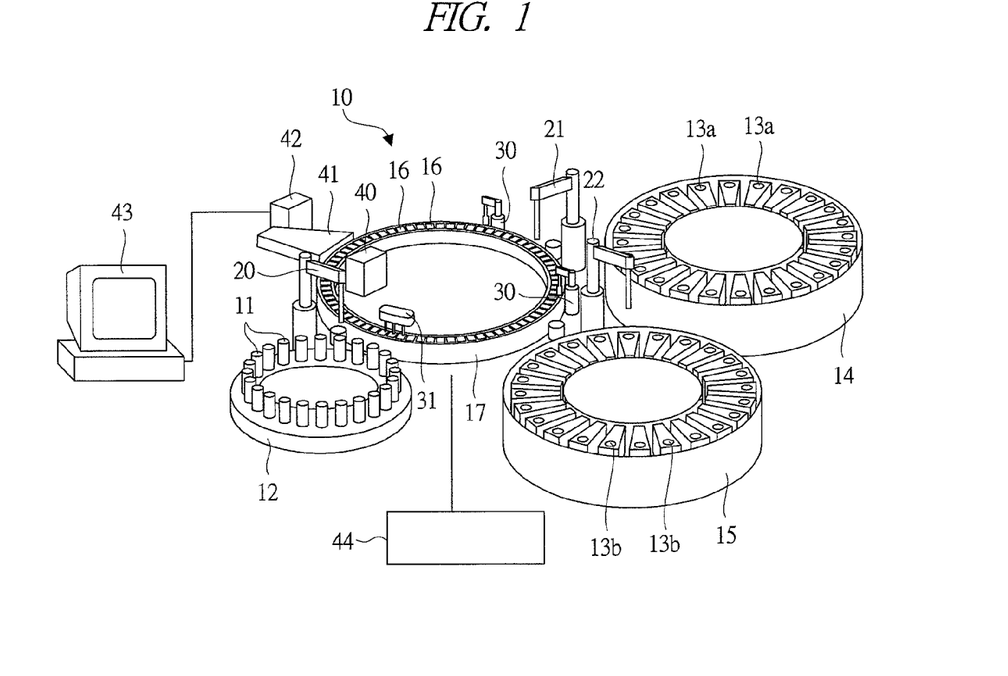
FIG. 1 is a schematic perspective view illustrating an outline of an embodiment of an automatic analysis device of the present invention.
Figure 2:
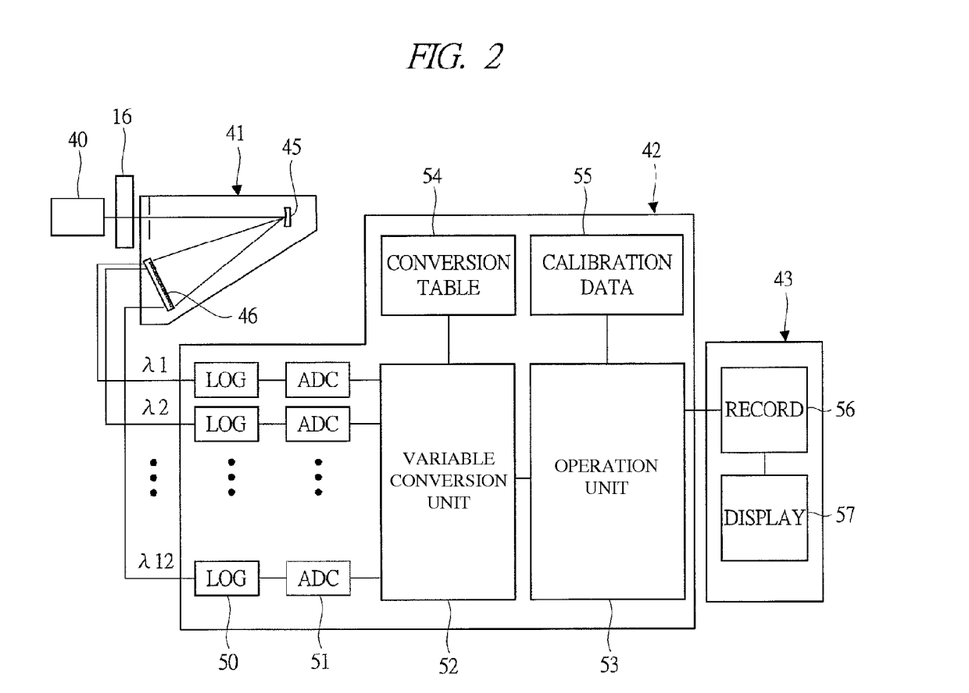
FIG. 2 is a configuration explanatory diagram explaining the configuration of a signal processing unit of the automatic analysis device of FIG. 1.

FIG. 1 is a schematic perspective view illustrating an outline of an embodiment of an automatic analysis device of the present invention, and FIG. 2 is a configuration explanatory diagram explaining a configuration of a signal processing unit of the automatic analysis device of FIG. 1.

As illustrated in FIG. 1, an automatic analysis device 10 includes: a sample disk 12 on which a plurality of sample containers 11 for holding a sample can be mounted; a first reagent disk 14 and a second reagent disk 15 on which a plurality of reagent containers 13a and 13b for holding a first reagent and a second reagent can be mounted, respectively; and a reaction disk 17 on which a plurality of reaction containers 16 are arranged along its circumferential direction.

Between the reaction disk 17 and the sample disk 12, a sample probe 20 which dispenses (discharges) a sample sucked from the sample container 11 into the reaction container 16 is provided.

Between the reaction disk 17 and the first reagent disk 14 and between the reaction disk 17 and the second reagent disk 15, a first reagent probe 21 which dispenses a reagent sucked from a reagent container 13a in the first reagent disk 14 into the reaction container 16 and a second reagent probe 22 which dispenses a reagent sucked from a reagent container 13b in the second reagent disk 15 into the reaction container 16 are provided, respectively.

In a periphery of the reaction disk 17, two stirrers 30 which stir liquid in the reaction containers 16 after dispensing the first reagent and the second reagent, respectively, a light source 40 by which light is passed through the reaction container 16, and a container cleaning mechanism 31 which cleans the reaction container 16 are provided in this order in a rotation direction of the reaction disk 17.

A spectroscopic optical system (detector) 41 is provided at a position facing the light source 40 so as to sandwich the reaction disk 17 therebetween. In a vicinity of the spectroscopic optical system, a signal processing circuit 42 which processes signals from the spectroscopic optical system 41 is provided. And, the signal processing circuit 42 is connected to a computer 43. Also, the automatic analysis device 10 also includes a controller 44 which controls an operation of the whole analyzer and exchanges a data to/from an outside.

As illustrated in FIG. 2, a diffraction grating 45 and an array sensor 46 composed of 12 pieces of a light-receiving element are installed inside the spectroscopic optical system 41, and a plurality of signal lines are connected from the array sensor 46 to the signal processing circuit 42. Inside the signal processing circuit 42, a plurality of logarithm amplifiers 50, a plurality of AD (analog/digital) converters 51, a variable conversion unit 52, an operation unit (calculating means) 53, a conversion table 54, and calibration data 55 are stored. The computer 43 includes a recording unit 56 and a display unit 57.

The automatic analysis device 10 operates as follows. A sample of a test object such as blood is placed in the sample container 11, and is set on the sample disk 12. A type of the analysis required for each sample is inputted to the controller 44.

The sample is collected by the sample probe 20, and a certain amount of the sample is dispensed into the reaction container 16 arranged on the reaction disk 17. Into the reaction container 16 into which the sample has been dispensed, a certain amount of the first reagent is dispensed by the first reagent probe 21 from the reaction container 13a installed on the first reagent disk 14. Also, as required, a certain amount of the second reagent is dispensed thereinto by the second reagent probe 22 from the reagent container 13b installed on the second reagent disk 15. Then, the sample and the reagent dispensed into the reaction container 16 are stirred by the stirrer 30.

The reaction disk 17 periodically repeats rotation and stop, and the light is passed through the reaction container 16 from the light source 40 for the photometry at a timing when the reaction container 16 is passed in front of the light source 40. The photometry is repeated during a reaction time of 10 minutes after the sample dispensing, and then, a reaction liquid in the reaction container 16 is ejected and the reaction container is cleaned by the container cleaning mechanism 31. During this process, in another reaction container 16, an operation with using another sample and another reagent is parallely performed.

The light from the light source 40 has a wide wavelength in a range from ultraviolet rays to infrared rays. The light passed through the reaction container 16 is entered into the spectroscopic optical system 41, is wavelength-separated by the diffraction grating 45, and is detected by the array sensor 46. Photocurrents having respective wavelengths from λ1 to λ12 are outputted from respective light-receiving elements of the array sensor 46, and are logarithmically converted by the respective logarithm amplifiers 50 in the signal processing circuit 42. Each logarithm amplifier 50 has a photocurrent value in a case of no light absorption in the reaction container 16 as a reference value, and an output of each logarithm amplifier is proportional to the absorbance. That is, the signals of the wavelengths from λ1 to λ12 are converted to the absorbances. Here, the absorbance is expressed by a logarithm of an attenuation rate of light intensity, which is a value obtained by multiplying a common logarithm of light transmittance in a length of 10 millimeters by −1, and a unit of the absorbance is "ABS". The output of the logarithm amplifier 50 is converted by the AD converter 51 into a digital value which is proportional to the absorbance.

The output converted into the digital value by the AD converter is converted into a secondary parameter by using the previously-defined conversion table 54 in the variable conversion unit 52. Here, the secondary parameter in the present invention is referred to as one parameter calculated by using values of a plurality of absorbances.

Specifically, in the variable conversion unit 52, the wavelength dependency of the absorbance is converted into a function "h(λ)" expressed by linear combination as a synthesis of a function "f(λ)" for expressing a wavelength dependency of a signal component and a function "g(λ)" for expressing a wavelength dependency of a noise component as shown by the following expressions.

$$f(\lambda)=\exp(-k\lambda)$$

$$g(\lambda)=\text{constant value}$$

$$h(\lambda)=A \cdot f(\lambda)+B \cdot g(\lambda)$$

In the expression, a symbol "k" is a coefficient representing a gradient of the wavelength dependency of the absorption caused by the aggregation, is set to a different value for each analysis item, and is previously stored in the conversion table 54. Symbols "A" and "B" are undetermined coefficients.

The values of A and B are determined by a weighted least square method so that differences between the function $h(\lambda)$ and the values of the absorbances at the wavelengths $\lambda 1$ to $\lambda 12$ inputted from the AD converters 51 are minimized, and the value of A is outputted to the operation unit 53 as the secondary parameter. A weighting coefficient "W" used in the weighted least square method is stored in the conversion table 54 as a value depending on a wavelength "$\lambda$" and an absorbance "ABS". As a simple example, with using a previously-determined absorbance upper limit "ABSmax" as a reference, when a value of W is set to 0 if the absorbance is equal to or higher than ABSmax and is set to 1 if the absorbance is less than ABSmax, a measurement value at a wavelength where the absorbance is higher than the previously-determined value is not used for calculating the concentration.

In the operation unit 53, by using the stored calibration data 55 which is obtained by previously examining a relationship between a concentration of a measured material (predetermined component) and a value, a change amount, or a change gradient of the secondary parameter at a specific timing in the reaction process, the value is converted into the value of the concentration based on the relationship and is outputted (calculated). The secondary parameter at the specific timing is obtained at, for example, each time of the measurement of a plurality of times of the measurement in the process of the reaction progress in the reaction container. Also, a relationship with the concentration may be linear, or may be curved as expressed by a spline function. The outputted concentration value is recorded in the recording unit 56 of the computer 43 and is displayed on the display unit 57.

Since the $f(\lambda)$ is provided by the logarithm function of the wavelength, the secondary parameter is preferably used as an item in the case of measuring the aggregation of fine particles such as the latex agglutination or the immunonephelometry, that is the case of measuring the concentration of the measured material based on the light absorption caused by the aggregation substances containing the material. Examples of such a preferred data are illustrated in FIGS. 3 and 4.

Figure 3:
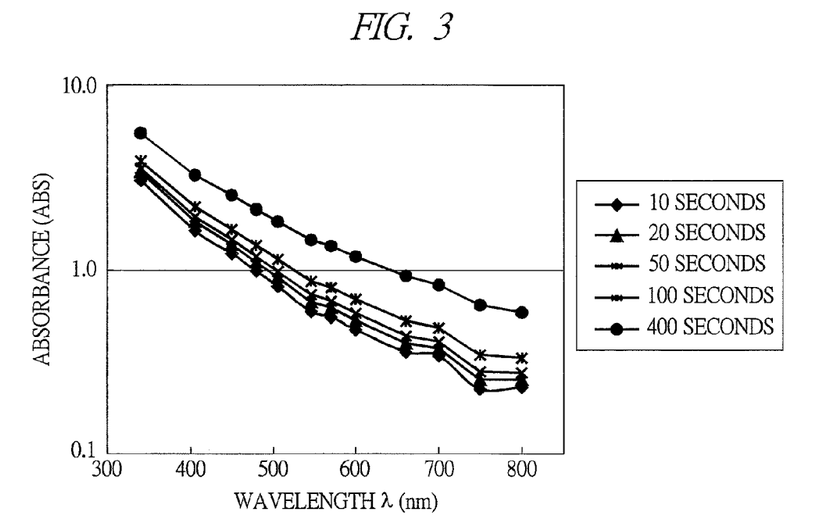
FIG. 3 is a graph illustrating a result obtained by measuring change in an absorbance at each wavelength with using latex agglutination.

FIG. 3 is a graph illustrating a result obtained by measuring the change in the absorbance at each wavelength in a case of using the Nanopia CRP produced by Sekisui Medical Co., Ltd. which is the reagent for the latex agglutination. Its horizontal axis represents the wavelength, and its vertical axis represents the absorbance indicated by a logarithm scale. As illustrated in FIG. 3, the absorbances indicated by the logarithm scale form a right-downward curve with respect to the wavelengths, and the curve substantially parallely rises along with the reaction progress after adding the reagent. A gradient of the curve is gentle on a long-wavelength side, and this is because of the detection error and the influence of the noise in the range of the small absorbance.

Figure 4:
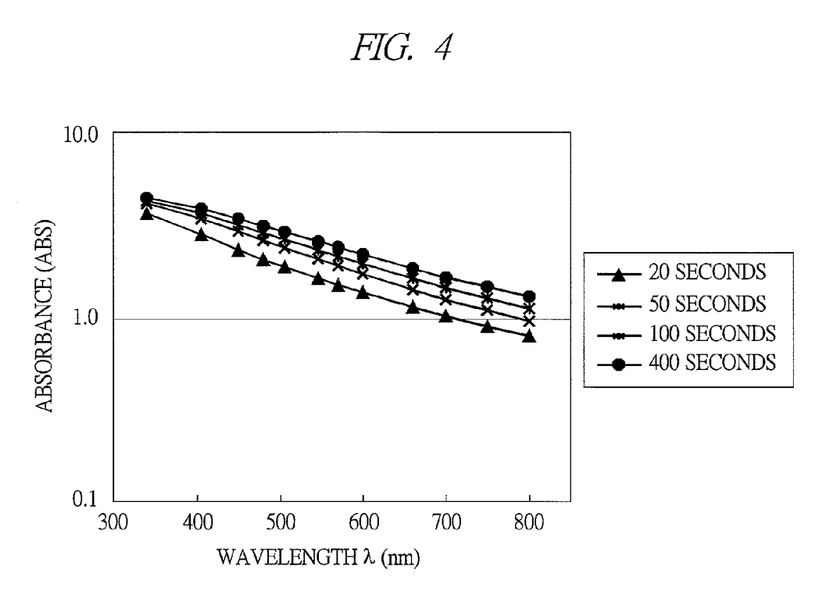
FIG. 4 is a graph illustrating a result obtained by measuring change in an absorbance at each wavelength with using immunonephelometry.

FIG. 4 is a graph illustrating a result obtained by measuring the change in the absorbance at each wavelength in a case of using Pureauto S IgG produced by Sekisui Medical Co., Ltd. which is the reagent for the immunonephelometry. In FIG. 4, similarly to FIG. 3, the absorbances form a right-downward curve with respect to the wavelengths, and the curve substantially parallely rises along with the reaction progress after adding the reagent. The absorbances are totally higher than those of FIG. 3, and the gradient with respect to the wavelengths is also different. There is a tendency that the absorbances are not on a straight line on a short-wavelength side, and this is because of the limitation of the detection range, the prozone phenomenon, or others.

Figure 5:
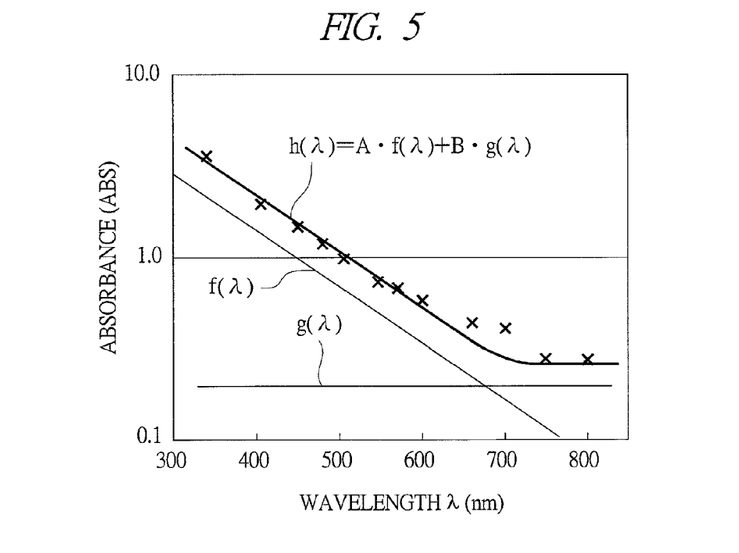
FIG. 5 is a graph illustrating a result obtained by converting a data at 100 seconds after adding a reagent in FIG. 3 to a function h(λ)

An actual attempt to convert one piece of the data to the $h(\lambda)$ has been made. This result is illustrated in FIG. 5. Note that FIG. 5 is a graph illustrating a result obtained by applying the conversion into the $h(\lambda)$ to a data at 100 seconds after adding the reagent in FIG. 3.

As illustrated in FIG. 5, it is found out that the linear combination of the function $h(\lambda)$ obtained by the conversion of the value of each absorbance is extremely close to the plotting of the value of each absorbance and the accuracy thereof is high.

In this manner, in the first embodiment, since the secondary parameter is calculated by using the values of the absorbances at the plurality of wavelengths, the high-accuracy concentration analysis can be achieved. That is, although it is considered that the noise is mixed in the value of the absorbance at each wavelength, the influence of each noise can be reduced by calculating the secondary parameter by using the values of the absorbances at the plurality of wavelengths, and therefore, the high-accuracy concentration analysis can be achieved.

Also, in the first embodiment, since the coefficient A of the function $f(\lambda)$ for expressing the signal and the coefficient B of the function $g(\lambda)$ for expressing the noise are obtained by the least square method, the influence of the noise on the value of the A used as the secondary parameter is small even when the noise added to the signals at all of the wavelengths is contained such that air bubbles are in the reaction container 16, and therefore, the high-accuracy concentration analysis can be achieved. Particularly, in this case, since the $g(\lambda)$ is the constant value, the wavelength characteristic of the light absorption caused by big air bubbles or others is matched with the function, and therefore, the influence of the noise can be effectively removed.

Further, in the first embodiment, since the weighted least square method in which the weighting function is reduced is used for the absorbance at the wavelength where the absorption rate is high, the influence of the wavelength is small even when the absorbance reaches a detection upper limit at a part of the wavelengths because of the high concentration of the measured material or even when the absorbance cannot be correctly measured because of the prozone effect or others, and therefore, the accurate analysis can be achieved up to the range of the high concentration.

Still further, in the first embodiment, since the signal at the short wavelength where the absorbance is large is used, the high-sensitivity analysis can be achieved even when the concentration is low and the absorbance at the long wavelength is small, and therefore, the high-sensitivity analysis can be achieved even at the low concentration.

Still Further, in the first embodiment, since the function $f(\lambda)$ for expressing the signal is provided by the exponential function whose coefficient is negative, the wavelength characteristic of the light attenuation caused by particles whose diameters are smaller than a light wavelength, which is calculated by the Mie scattering theory for light scattering or others is matched with the function. Therefore, the secondary parameter can be reproducibly calculated so as to be matched with the wavelength distribution of the absorbances caused by the aggregation particles. And, since the coefficient at this time can be individually determined for each item, the analysis can be also adapted to a system in which the diameter and concentration of the aggregation particles are different, and therefore, the high-accuracy and wide-measurement-range analysis can be achieved in various types of analysis.

Still further, in the first embodiment, since the calibration data 55 for the calibration curve with respect to the known concentrations is obtained for not the absorbance at each wavelength but the secondary parameter, the operation of obtaining the calibration curve can be simplified, and besides, a consistent calibration curve which is not switched at an intermediate part can be obtained, and therefore, the high-accuracy concentration analysis can be achieved.

Still further, in the first embodiment, since the calibration curve with respect to one secondary parameter is used, the calibration curve with not only the linear relationship but also a curved relationship such as expressed by a spline function can be also easily used, and therefore, the invention can be adapted for the analysis with using various types of reactions. Moreover, the analysis in a wide concentration range from a low concentration to a high concentration can be accurately achieved.

Still further, in the first embodiment, since the analysis in the wide concentration range from the low concentration to the high concentration can be achieved by one time of measurement, there is no need to change the reagent or the dispensing amount depending on the difference in the concentration, and therefore, the number of times of analysis can be reduced, and the analysis can be achieved at a low cost.

In the first embodiment described above, the function $g(\lambda)$ for expressing the noise is the constant value, and this is because the light attenuation due to the air bubbles or others becoming the noise source does not have the wavelength dependency when the particle diameter is larger than several times the wavelength according to the Mie scattering theory or others. Therefore, for the $g(\lambda)$, a function to which the wavelength dependency of the serum color is introduced may be set instead of the constant value, or a plurality of functions to which a plurality of wavelength dependencies are introduced may be used at the same time.

Still further, in the first embodiment, since the $f(\lambda)$ is provided by the logarithm function of the wavelengths, the invention can be easily adapted to the case of measuring the aggregation of the fine particles such as the latex agglutination and the immunonephelometry. However, the invention is not limited thereto. For example, in analysis for a color reaction with using an enzyme reaction or others, when a function matched with the wavelength characteristic of the absorbance of the color reaction is used as the $f(\lambda)$, the high-accuracy analysis with small influence of the noise can be achieved even in the color reaction.

Still further, in the analysis of the color reactions, a conventional method of using the difference between the absorbances at two wavelengths can be also used. In that case, the difference between the absorbances at the two wavelengths can be used as the secondary parameter.

Second Embodiment

A second embodiment of the present invention is similar to the first embodiment except for a point that the calculation method in the variable conversion unit 52 is different from each other, and therefore, the explanation for the similar matters will be omitted as much as possible.

In the second embodiment, by the variable conversion unit 52, a secondary parameter "Pa2" is calculated as follows by using a function "$D(\lambda, \lambda 12)$" defined by the difference between the absorbance "$ABS(\lambda)$" of each wavelength "$\lambda$" and the absorbance "$ABS(\lambda)$" of the longest wavelength "$\lambda 12$", a weighting function "$W(\lambda)$", and a gain function "$G(\lambda)$".

$$Pa2=W(\lambda 1)G(\lambda 1)D(\lambda 1,\lambda 12)+W(\lambda 2)G(\lambda 2)D(\lambda 2,\lambda 12)+\ldots+W(\lambda 11)G(\lambda 11)D(\lambda 11,\lambda 12)$$

Here, the following is set.

$$D(\lambda i,\lambda j)=ABS(\lambda i)-ABS(\lambda j)$$

$$W(\lambda 1)+W(\lambda 2)+\ldots+W(\lambda 11)=1$$

$$G(\lambda)=C\cdot\exp(k\lambda)$$

The "C" is a constant.

A value of the $W(\lambda)$ also depends on the absorbance, and is changed so as to be small at a wavelength where the absorbance is relatively large or small and be large at a wavelength between the wavelengths where the absorbance is large and small. That is, the value of the $W(\lambda)$ is determined by using the conversion table 54 so as to be small at a wavelength where the absorbance exceeds a set upper limit and to be larger as shortening the wavelength in a range where the absorbance does not exceed the upper limit. The value of the $k$ is also stored in the conversion table 54 as a different value for each measurement item. The processing after performed in the operation unit 53 is similar to that of the first embodiment.

As described above, in the second embodiment, since the noise mixed in the value of the absorbance at each wavelength is cancelled by subtracting a value of an absorbance at another wavelength from the value of the absorbance at the wavelength, the high-accuracy analysis with small influence of the noise can be achieved.

Also, in the second embodiment, since the absorbance at the longest wavelength where the light absorption caused by the aggregation particles is the smallest is used for cancelling the noise, only the absorbance corresponding to the noise can be efficiently removed, and loss of the absorbance corresponding to the signal is small, and therefore, the high-accuracy analysis can be achieved. Note that it goes without saying that another wavelength can be selected instead of the longest wavelength depending on the wavelength characteristic of the apparatus or the characteristics of the measurement item.

Still furthermore, in the second embodiment, since the weighting function at the wavelength where the absorbance exceeds the upper limit is decreased, the error due to the detection limit or the prozone can be reduced even when the amount of the aggregation substances containing the measured material at the high concentration is large, and therefore, the high-accuracy analysis can be achieved up to the high-concentration range.

Still further, in the second embodiment, since the value of the weighting function at the high-sensitive short wavelength is increased at the wavelength where the absorbance is equal to or lower than the upper limit, the high-sensitive analysis can be achieved even in the low-concentration measurement.

Still further, in the second embodiment, since the gain function $G(\lambda)$ is provided by the function which is the inverse of the wavelength characteristic of the absorption caused by the particles each having the smaller wavelength than the wavelength of the light, the gradient of the relationship between the concentration of the aggregation substances and the secondary parameter is the same with respect to any wavelength, and therefore, the concentration of the aggregation substances and the secondary parameter have the proportional relationship regardless of the distribution of the weighting function. That is, since the gradients are different depending on the wavelength, the gradients are adversely different from each other if they are similarly averaged. Accordingly, by using the fact that the gradient is expressed by the exponential function, the G(λ) is multiplied as the function depending on the wavelength so as to correct the gradients, so that one calibration curve can be obtained so that the gradients are corrected to be the same. In this manner, the concentration calculation by using the secondary parameter can be achieved at the high accuracy in the wide range.

Still further, in the second embodiment, since the secondary parameter is obtained by the summation of the data of the absorbances at the plurality of wavelengths with using the weighting function, there is the effect of averaging and reducing the noise contained in each wavelength, and therefore, the high-accuracy analysis with small influence of the noise can be achieved.

Still further, in the second embodiment, since the coefficient k of the gain function can be adjusted in accordance with the item, the invention can be effectively used for the object in the wide scope including the latex agglutination and the immunonephelometry.

Still further, in the second embodiment, since the calculation for the secondary parameter is not complicated as using the least square method but is simple, the volume of the calculation in the variable conversion unit 52 is small, and therefore, the high-speed processing can be achieved.

In the second embodiment explained above, even the conventional two-wavelength differential analysis with using the main wavelength λi and the sub wavelength λj can be also applied by setting the W(λi) and the other W(λ) to 1 and 0, respectively, and therefore, the invention can be widely adapted to the measurement items including the color reaction.

In the foregoing, the present invention made by the inventors has been concretely described based on the first and second embodiments. However, it is needless to say that the present invention is not limited to the foregoing embodiments and various modifications can be made within the scope of the present invention.

For example, in the above-described first and second embodiments, the concentration of the measured material is calculated based on the relationship with the secondary parameter. However, the calculation may be not based on the secondary parameter as long as the concentration is calculated by using the absorbances at the plurality of wavelengths based on the light absorption caused by the aggregation substances and the absorbance at the wavelength to which the noise component is reflected. Specifically, the concentration may be directly calculated by the neural network or others from the inputted value of the absorbance at the wavelength without calculating the intermediate parameter.

Also, in the above-described first and second embodiments, the wavelengths used in the calculation for the concentration of the measured material are 12 wavelengths from λ1 to λ12. However, the wavelengths may be more or less than the 12 wavelengths as long as they are a plurality of wavelengths such as three wavelengths.

Still further, in the above-described first and second embodiments, the variable conversion unit 52, the operation unit 53, the conversion table 54, and the calibration data 55 are embedded inside the signal processing circuit 42. However, they may be not embedded inside the signal processing circuit 42, and their functions may be achieved as being softwares by converting them to the secondary parameter inside the computer 43 by using a conversion expression. When they are embedded inside the signal processing circuit 42, there is a merit that a volume of signals transferred to the computer 43 and a volume of calculations required for the computer 43 are small. When their functions are performed by the computer 43, there are merits that a structure of the signal processing circuit 42 can be simplified, the operation algorithm can be easily changed, and others.

EXAMPLES

Hereinafter, the present invention will be further explained by Examples. Note that the present invention is not limited by these Examples.

Figure 6:
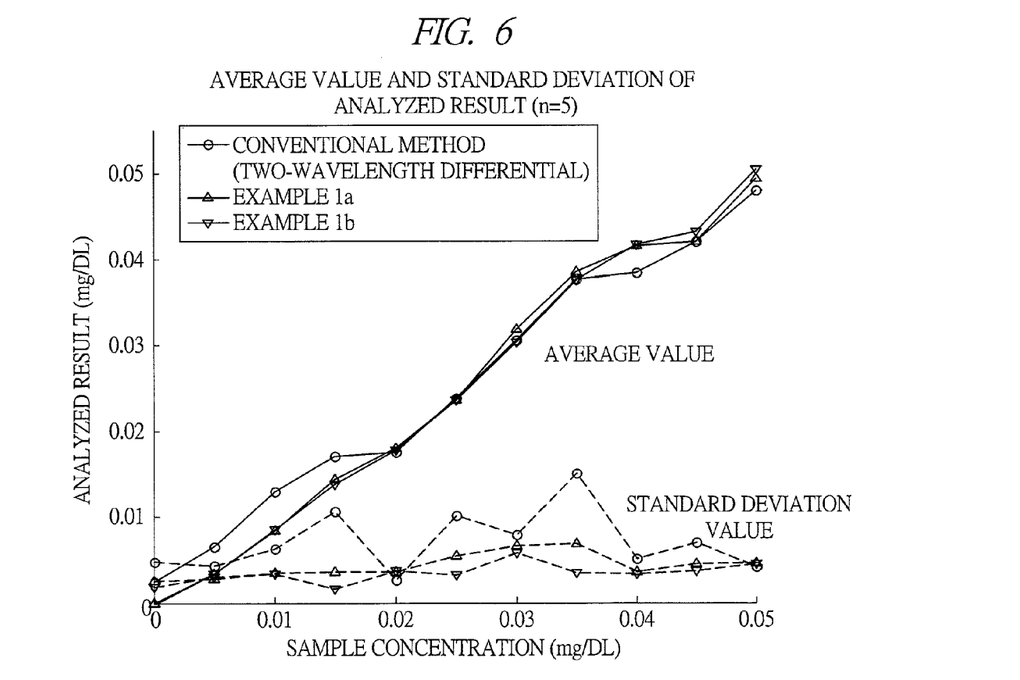
FIG. 6 is a graph illustrating a result obtained by examining a noise reduction effect in a case of applying actual analysis to the first embodiment.

FIG. 6 plots an analysis result according to a conventional method and the method of the first embodiment in a case of using the Nanopia CRP produced by Sekisui Medical Co., Ltd. as the reagent and applying a low-concentration control serum of the CRP for the sample. A horizontal axis shows a concentration of the sample, and a vertical axis shows the analysis result. In the conventional method, the two-wavelength difference between the main wavelength of 570 nm and the sub wavelength of 800 nm is used, and the concentration is converted by using a difference in two times of measurement at 45 seconds and 300 seconds after starting the reaction and using a value calibrated for the known samples each having concentrations of 0 mg/dL and 0.05 mg/dL.

In the first embodiment, it is required to determine the value of the k and the weighting coefficient W, and two types of combination are attempted for them. The measurement wavelengths λ are 12 wavelengths of 340, 405, 450, 480, 505, 546, 570, 600, 660, 700, 750, and 800 nm. In an Example 1a, k=0.088, and the weighting coefficient W is expressed by exp(kλ) for each wavelength except for 340 nm. In an Example 1b, in the weighting function W of the Example 1a, the weighting is further increased for the wavelengths of 405, 700, and 800 nm. Also in these cases, similarly to the conventional method, the measurement is performed twice at 45 seconds and 300 seconds after starting the reaction, and the concentration is converted by using a difference between the respective calculated secondary parameters and using a value calibrated for the known samples each having concentrations of 0 mg/dL and 0.05 mg/dL.

An experiment for the measurement has been performed five times for each of samples having 11 types of concentrations from 0 to 0.05 mg/dL. In order to understand the influence of the noise, an environment in which many air bubbles are floated outside the reaction container is produced, and the extracted noise component is added to the data. The plotted analysis results are illustrated as a graph of FIG. 6. An average value at each concentration is indicated by a solid line, and its standard deviation value is indicated by a broken line. As seen from the graph, compared with the conventional method, the linearity of the average values is improved, and the standard deviation values are also reduced, and therefore, the noise is difficult to affect the data. In this data, while the average of the standard deviation values is 0.0071 mg/dL in the conventional method, the average in the Example 1a is 0.0043 mg/dL and the average in the Example 1b is 0.0034 mg/dL. The effect of the noise influence reduction compared with that of the conventional method is 39% and 55% in the Examples 1a and 1b, respectively.

In the case of the Example 1a, the weighting coefficient W is proportional to an inverse number of the absorbance expected at each wavelength. In this manner, when the value of A is calculated by the least square method, it is avoided to calculate the data of the wavelength where the absorbance is large with a large weight, and the data of the plurality of wavelengths can be treated with equal effects, and therefore, the effect of the noise influence reduction can be increased.

Also, in the cases of the Examples 1a and 1b, since the weighting coefficient for the data of the wavelength of 340 nm where the noise is large due to small light intensity is set to 0, the high-accuracy analysis can be achieved without the influence of the wavelength where the noise is large.

Still further, in the case of the Example 1b, since the weighting coefficient for the wavelength where the influence of the noise is particularly small is further increased, the high-sensitivity analysis in which the influence of the noise is further reduced than that of the Example 1a can be achieved.

Figure 7:
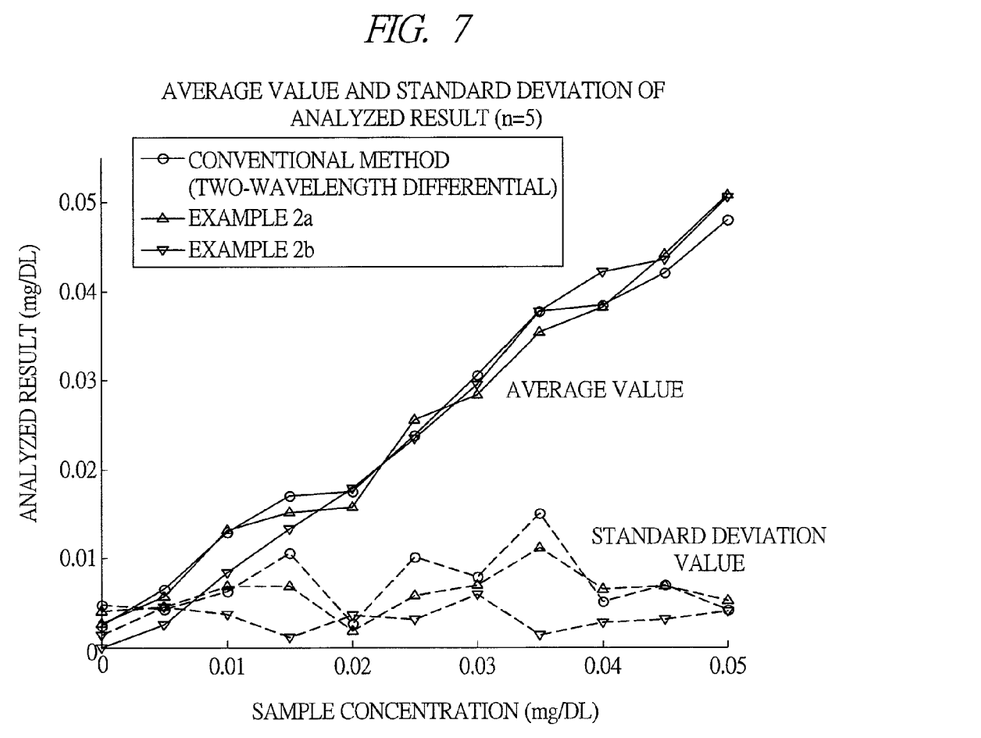
FIG. 7 is a graph illustrating a result obtained by examining a noise reduction effect in a case of applying actual analysis to a second embodiment.

FIG. 7 plots an analysis result according to the conventional method and the method of the second embodiment for the measurement used in FIG. 6. In the second embodiment, it is required to determine the value of k, the weighting function $W(\lambda)$, the gain function $G(\lambda)$, and a constant C, and two types of combination are attempted for them. In an Example 2a, k=0.088, and the weighting function $W(\lambda)$ is provided as 1 for the wavelengths except for 340 nm. In an Example 2b, the weighting function $W(\lambda)$ is provided as a different value for each of the wavelengths. Also in these cases, similarly to the conventional method, the measurement is performed twice at 45 seconds and 300 seconds after starting the reaction, and the concentration is converted by using a difference between the respective calculated secondary parameters and using a result calibrated for the known samples each having the concentrations of 0 mg/dL and 0.05 mg/dL.

In the view of FIG. 7, compared with the conventional method, the linearity is improved, and its standard deviation value is also reduced, and therefore, the noise is difficult to affect the data. In this data, while an average of the standard deviation values is 0.0071 mg/dL in the conventional method, the average is 0.0061 mg/dL in the Example 2a and is 0.0031 mg/dL in the Example 2b. The effect of the noise influence reduction compared with that of the conventional method is 14% and 56% in the Examples 2a and 2b, respectively.

In the cases of the Examples 2a and 2b, since the calculation for the secondary parameter is the simple arithmetic calculation, the noise reduction can be achieved by a small calculation volume, and therefore, a low-cost secondary parameter converter can be used.

INDUSTRIAL APPLICABILITY

The present invention can be used for an automatic analysis device automatically analyzing a component of blood or others.

The invention claimed is:

1. An automatic analysis device for measuring a component of a sample based on light absorption caused by latex agglutination or immunonephelometry, comprising:
   at least one reaction container;
   a sample probe discharging a sample into the reaction container;
   a reagent probe discharging a reagent into the reaction container;
   a light source irradiating light through the reaction container;
   a detector detecting light transmitted from the light source through the reaction container, for separating the light into a plurality of wavelengths, and for outputting a plurality of photocurrents, each photocurrent associated with a respective wavelength; and
   a signal processing circuit, coupled to the detector, configured to calculate a concentration of a predetermined component in the sample, including:
      logarithm amplifiers configured to convert the plurality of photocurrents to a plurality of absorbance values,
      analog-to-digital converters, coupled to the logarithm amplifiers, configured to digitize the plurality of absorbance values,
      a conversion table configured to store data corresponding to coefficient k representing a gradient of the wavelength dependency of the absorption caused by the aggregation, which is set to a different value for each predetermined component, the conversion table further configured to store data corresponding to A and B coefficients obtained by the least square method,
      a calibration table configured to store calibration data obtained by previously examining a relationship between a concentration of a predetermined component and a value, a change amount, or a change gradient of the secondary parameter at a specific timing in the reaction process,
      a variable conversion unit, coupled to the analog-to-digital converters and conversation table, configured to convert the digitized absorbance values to a secondary parameter, $h(\lambda)$, using a linear combination of a signal function $f(\lambda)=\exp(-k\lambda)$ and a noise function $g(\lambda)$=a constant value caused by air bubbles in the sample,
      the secondary parameter governed by the equation:

$h(\lambda)=A \cdot f(\lambda)+B \cdot g(\lambda)$, and an operation unit, coupled to the variable conversion unit, for determining the concentration of the predetermined component based on the secondary parameter by using the stored calibration data in the calibration table.

2. The automatic analysis device according to claim 1, wherein the negative coefficient is set to a different value depending on a type of measurement.

3. The automatic analysis device according to claim 1, wherein an absorbance value at a wavelength where the absorbance value is higher than a previously-determined absorbance value is not used for calculating the concentration of the predetermined component.

4. The automatic analysis device according to claim 1, wherein a plurality of times of measurement are performed in a process of reaction progress in the reaction container to previously examine a relationship between the concentration and a value, a changed amount, or a change gradient of the secondary parameter obtained in each time of the measurement, so that the concentration of the predetermined component in the sample is calculated based on the relationship.

* * * * *